United States Patent [19]

Takaya et al.

[11] Patent Number: 4,487,768
[45] Date of Patent: Dec. 11, 1984

[54] CEPHEM COMPOUNDS

[75] Inventors: Takao Takaya, Kawanishi; Takashi Masugi, Ikeda; Hisashi Takasugi, Hamaguchinishi; Kenzi Miyai, Kawanishi, all of Japan

[73] Assignee: Fujisawa Pharmaceutical Co., Ltd., Osaka, Japan

[21] Appl. No.: 452,301

[22] Filed: Dec. 22, 1982

[51] Int. Cl.³ .................. A61K 31/545; C07D 501/46
[52] U.S. Cl. ........................................ 424/246; 544/22
[58] Field of Search ........................... 424/246; 544/22

[56] References Cited

U.S. PATENT DOCUMENTS

| 4,033,950 | 7/1977 | Cook et al. | 544/22 |
|---|---|---|---|
| 4,328,225 | 5/1982 | Vignau et al. | 544/22 |
| 4,381,299 | 4/1983 | Teraji et al. | 544/22 |

FOREIGN PATENT DOCUMENTS 2018758A 10/1979 United Kingdom .

Primary Examiner—Paul M. Coughlan, Jr.
Attorney, Agent, or Firm—Oblon, Fisher, Spivak, McClelland & Maier

[57] ABSTRACT

The invention relates to novel compounds of high antimicrobial activity of the formula:

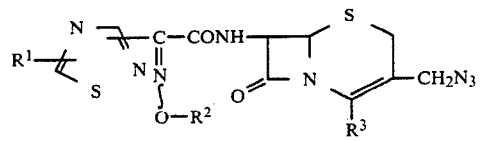

wherein
$R^1$ is amino or protected amino,
$R^2$ is carboxy(lower)alkyl or protected carboxy(lower)alkyl, and
$R^3$ is carboxy or protected carboxy,
and a pharmaceutically acceptable salt thereof.

3 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms, especially for oral administration.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases cuased by pathogenic bacteria in human being and animals.

The object new cephem compounds are novel and can be represented by the following general formula:

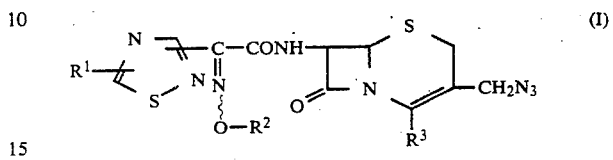

wherein
$R^1$ is amino or protected amino,
$R^2$ is carboxy(lower)alkyl or protected carboxy(lower)alkyl, and
$R^3$ is carboxy or protected carboxy.

According to the present invention, the new cephem compounds (I) can be prepared by various processes which are illustrated in the following schemes.

Process 1

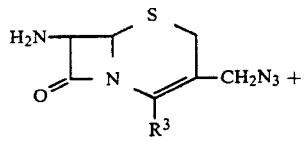

(II)

or its reactive
derivative at the amino
group or a salt thereof

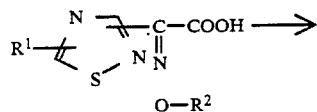

(III)

or its reactive derivative
at the carboxy group or a
salt thereof

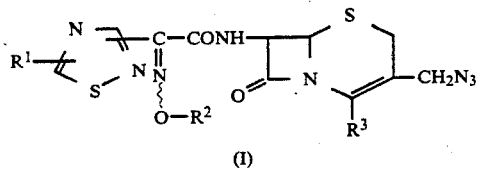

(I)

or a salt thereof

Process 2

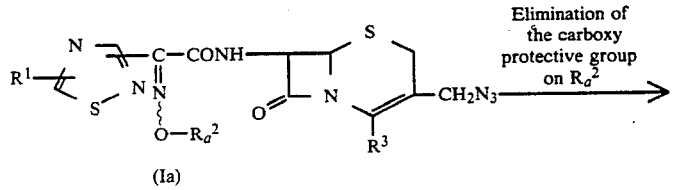

(Ia)

or a salt thereof

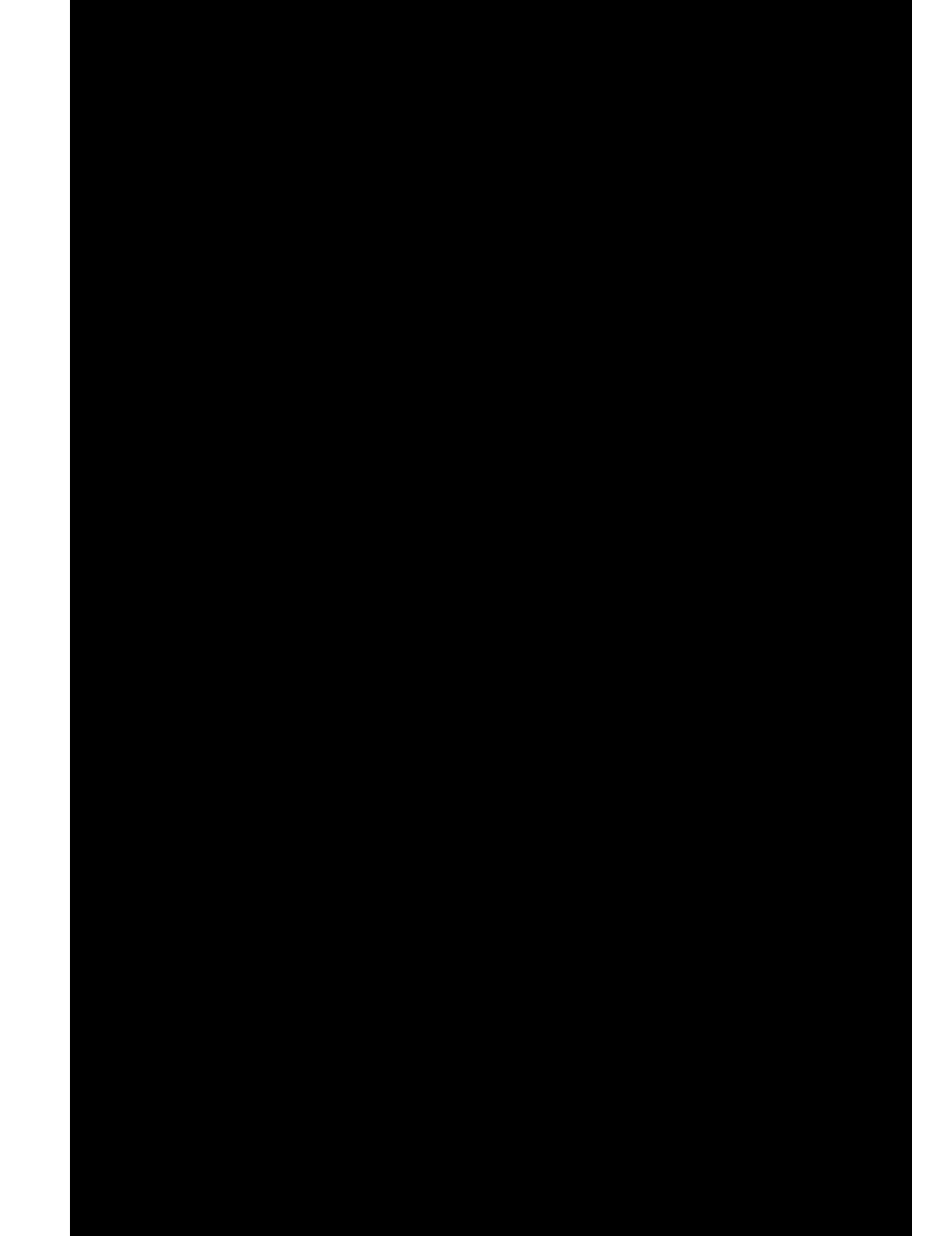

isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "lower alkyl moiety" in the terms "carboxy(lower)alkyl" and "protected carboxy(lower)alkyl" may include methyl, ethyl, propyl, isopropyl, butyl, t-butyl, pentyl, hexyl and the like.

Preferable example of carboxy(lower)alkyl may include carboxymethyl, 1-carboxyethyl, 2-carboxyethyl, 1-carboxypropyl, 2-carboxypropyl, 3-carboxypropyl, 4-carboxybutyl, 5-carboxypentyl, 6-carboxyhexyl, 1-carboxyisopropyl, 1-ethyl-1-carboxyethyl, 2-methyl-2-carboxypropyl, and the like.

Preferable example of protected carboxy(lower)alkyl may include esterified carboxy(lower)alkyl, and more preferably lower alkoxycarbonyl(lower)alkyl (e.g. methoxycarbonylmethyl, ethoxycarbonylmethyl, propoxycarbonylmethyl, tert-butoxycarbonylmethyl, 2-ethoxycarbonylethyl, 2-ethoxycarbonylpropyl, 4-ethoxycarbonylbutyl, 1-tert-butoxycarbonylisopropyl, 1-tert-butoxycarbonyl-1-methylpropyl, 4-tert-butoxycarbonylbutyl, 5-tert-butoxycarbonylpentyl, 6-butoxycarbonylhexyl, etc.) and the like.

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, trimethylsilylacetamide or the like; a derivative formed by reaction of the compound (II) with phosphorus trichloride or phosgene, and the like.

Suitable salt of the compounds (II) and (III) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [(CH$_3$)$_2$N$^+$=CH—]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)-alkylmorphorine, N,N-di(lower)alkylbenzylamine, or the like. The reaction temperature is not critical, and the reaction is usually carried out under cooling or at ambient temperature.

PROCESS 2

The object compound (Ib) or a salt thereof can be prepared by subjecting the compound (Ia) or a salt thereof to elimination reaction of the carboxy protective group on R$_a^2$.

Suitable salts of the compounds (Ia) and (Ib) can be referred to the one exemplified for the compound (I).

In the present elimination reaction, all conventional methods used in the elimination reaction of the carboxy protective group, for example, hydrolysis, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsabstituted ar(lower)alkyl ester or lower alkyl ester and carried out by reacting the compound (Ia) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. A liquid acid can also be used as the solvent. These solvents may be used as a mixture thereof. The reaction temperature is not critical, and the reaction is usually carried out under cooling, at ambient temperature or under warming.

In case that the object compound (I) is obtained in a form of the free acid at the 4-position and/or the oxime portion and/or in case that the object compound (I) has free amino group, it may be transformed into its pharmaceutically acceptable salt as aforementioned by a conventional method.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents, especially for oral administration. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives, such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol and the like.

While the dosage of the compounds will vary depending upon the age and condition of the patient, an average single dose of about 10 mg, 50 mg, 100 mg, 250 mg, 500 mg, and 1000 mg of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities, urinary excretion and biliary excretion of a representative compound of the present invention are shown below.

[1] Test Compound:
7-[2-Carboxymethoxyimino-2-(5-amino-1,2,4-thiadiazol-3-yl)acetamido]-3-azidomethyl-3-cephem-4-carboxylic acid (syn isomer).
(hereinafter referred to as Test Compound (1))

[2] Test:
(A) Minimal inhibitory concentration
 1 Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in tems of $\mu g/ml$ after incubation at 37° C. for 20 hours.

2 Test Results

| | MIC ($\mu g/ml$) |
| --- | --- |
| | Compound |
| Test strains | Test Compound (1) |
| Proteus mirabilis 18 | 0.05 |
| Proteus vulgaris 2 | 0.1 |

(B) Urinary excretion
 1 Test Method

Urine of rats was collected with a urine collector at 0 to 6, and 6 to 24 hours after oral administration of 100 mg/kg of the test antibiotic. The antibiotic levels in the urine samples were bioassayed with the standard solution prepared with M/15 phosphate buffer (pH 7.0) and the urinary recovery in 24 hours was calculated.

2 Test Result

| | Urinary recovery in 24 hours (%) |
| --- | --- |
| Test Compound (1) | 26.61 |

(C) Biliary excretion
 1 Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg/kg of the test antibiotic. The antibiotic levels in the bile samples were bioassayed with the standard solutions prepared with M/15 phosphate buffer (pH 7.0) and the biliary recovery in 24 hours were calculated.

2 Test Result

| | Biliary recovery in 24 hours (%) |
| --- | --- |
| Test Compound (1) | 4.72 |

The following examples are given for the purpose of illustrating the present invention in more detail.

EXAMPLE 1

To a suspension of phosphorus pentachloride (4.2 g) in methylene chloride (60 ml) was added 2-t-butoxycarbonylmethoxyimino-2-(5-amino-1,2,4-thiadiazol-3-yl)acetic acid (syn isomer) (6.05 g) under stirring at −18° C. The mixture was stirred for an hour at −15° to −12° C. Then, dry diisopropyl ether was added to the solution, the precipitates were collected by filtration and washed with dry diisopropyl ether. To the solution of 7-amino-3-azidomethyl-3-cephem-4-carboxylic acid (5.1 g) and trimethylsilylacetamide (18.4 g) in methylene chloride (50 ml) was added the precipitates obtained above at −10° C. under stirring. The reaction mixture was stirred for an hour at −10° to −5° C.

The reaction mixture was poured into water (100 ml) and extracted with ethyl acetate (100 ml). The organic layer was washed with 10% aqueous solution of sodium chloride, dried over magnesium sulfate and evaporated to give 7-[2-t-butoxycarbonylmethoxyimino-2-(5-amino-1,2,4-thiadiazol-3-yl)acetamido]-3-azidomethyl-3-cephem-4-carboxylic acid (syn isomer) (4.75 g).

IR (Nujol): 3270, 2100, 1770, 1720, 1680, 1620, 1520 cm$^{-1}$.

NMR (DMSO-d$_6$, δ): 1.45 (9H, s), 3.57 (2H, ABq, J=18 Hz), 3.86 and 4.40 (2H, Abq, J=13 Hz), 4.62 (2H, broad s), 5.12 (1H, d, J=5 Hz),
5.82 (1H, dd, J=5 Hz, 8 Hz), 8.03 (2H, broad s), 9.40 (1H, d, J=8 Hz).

EXAMPLE 2

The following compound was obtained according to a similar manner to that of Example 1.
7-[2-Carboxymethoxyimino-2-(5-amino-1,2,4-thiadiazol-3-yl)acetamido]-3-azidomethyl-3-cephem-4-carboxylic acid (syn isomer).
mp>300° C.
IR (Nujol): 3300, 3200, 2100, 1770, 1720, 1680, 1620, 1520 cm$^{-1}$.

EXAMPLE 3

Trifluoroacetic acid (18 ml) was added to a suspension of 7-[2-t-butoxycarbonylmethoxyimino-2-(5-amino-1,2,4-thiadiazol-3-yl)acetamido]-3-azidomethyl-3-cephem-4-carboxylic acid (syn isomer) (4.6 g) in methylene chloride (10 ml) and anisole (5 ml), and the mixture was stirred for 7 hours at ambient temperature. The reaction mixture was added dropwise to diisopropyl ether (200 ml) and precipitates were collected by filtration. The precipitates were added to a mixture of water and ethyl acetate, and the mixture was adjusted to pH 7.0 with saturated aqueous solution of sodium bicarbonate. The separated aqueous layer was adjusted to pH 3.0 with 10% hydrochloric acid. The precipitates were collected by filtration and successively washed with water to give 7-[2-carboxymethoxyimino-2-(5-amino-1,2,4-thiadiazol-3-yl)acetamido]-3-azidomethyl-3-cephem-4-carboxylic acid (syn isomer). (2.7 g).
mp>300° C.
IR (Nujol): 3300, 3200, 2100, 1770, 1720, 1680, 1620, 1520 cm$^{-1}$.

NMR (DMSO-d$_6$, δ): 3.57 (2H, broad s), 3.90 and 4.42 (2H, Abq, J=13 Hz), 4.63 (2H, s), 5.18 (1H, d, J=5 Hz), 5.83 (1H, dd, J=5 Hz, 8 Hz), 8.08 (2H, broad s), 9.50 (1H, d, J=8 Hz).

What we claim is:

1. A compound of the formula:

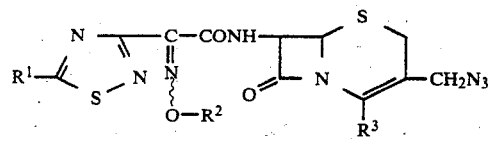

wherein
R$^1$ is amino or protected amino,
R$^2$ is carboxy(lower)alkyl or protected carboxy(lower)alkyl, and
R$^3$ is carboxy or protected carboxy,
and a pharmaceutically acceptable salt thereof.

2. A compound of claim 1, which is 7-[2-carboxymethoxyimino-2-(5-amino-1,2,4-thiadiazol-3-yl)acetamido]-3-azidomethyl-3-cephem-4-carboxylic acid (syn isomer).

3. An antibacterial composition comprising an effective amount of a compound of claim 1 in association with a pharmaceutically acceptable substantially non-toxic carrier or excipient.

* * * * *